(12) United States Patent
Balazs et al.

(10) Patent No.: US 8,586,100 B2
(45) Date of Patent: Nov. 19, 2013

(54) POPULATIONS OF HEMATOPOIETIC STEM CELLS

(75) Inventors: Alejandro Balazs, Berkeley, CA (US); Richard Mulligan, Cambridge, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 13/298,724

(22) Filed: Nov. 17, 2011

(65) Prior Publication Data

US 2012/0121552 A1    May 17, 2012

Related U.S. Application Data

(63) Continuation of application No. 10/577,177, filed as application No. PCT/US2004/036143 on Oct. 29, 2004, now Pat. No. 8,088,585.

(60) Provisional application No. 60/516,107, filed on Oct. 31, 2003.

(51) Int. Cl.
*A61K 35/28* (2006.01)
*C12N 5/08* (2006.01)

(52) U.S. Cl.
USPC .......................................... 424/577; 435/372

(58) Field of Classification Search
None
See application file for complete search history.

(56) References Cited

U.S. PATENT DOCUMENTS

| 7,153,501 B2 * | 12/2006 | Friedlander et al. ....... 424/93.21 |
| 2002/0064855 A1 * | 5/2002 | Lemischka et al. ........... 435/226 |
| 2004/0143863 A1 * | 7/2004 | Li et al. .......................... 800/18 |

FOREIGN PATENT DOCUMENTS

| WO | WO00/14203 | * | 3/2000 |
| WO | WO 03/068937 | | 8/2003 |

OTHER PUBLICATIONS

Crawley, J.T.B. et al., "Distribution of Endothelial Cell Protein C/Activated Protein C Receptor (EPCR) During Mouse Embryo Development," Thromb. Haemost, 88-259-66 (2002).
Esmon, C.T., "Structure and functions of the endothelial cell protein C receptor", Crit. Care Med., 32(5):S298-S301 (2004).
Ghannadan, M. et al., "Detection of Novel CD Antigens on the Surface of Human Mast Cells and Basophils," Int Arch Allergy Immunol, 127: 299-307 (2002).
Goodell, M.A. et al., "Isolation and Functional Properties of Murine Hematopoietic Stem Cells that are Replicating In Vivo", J Exp Med, 183: 1797-1806 (1996).
Gu, J.M., et al., "Disruption of the Endothelial Cell Protein C Receptor Gene in Mice Causes Placental Thrombosis and Early Embryonic Lethality," J. Biological Chemistry, 277(45); 43335-43343 (2002).
McNagny, K.M. et al., "Thrombomucin, a Novel Cell Surface Protein that Defines Thrombocytes and Multipotent Hematopoietic Progenitors," J. Cell Biology, 138(6):1395-1407 (1997).
Miyazato, A. et al., "Identification of myelodysplastic syndrome-specific genes by DNA microarray analysis with purified hematopoietic stem cell fraction," Blood, 98: 422-427 (2001).
Wognum, et al., "Identification and Isolation of Hematopoietic Stem Cells," Archives of Medical Research 34: 461-475 (2003).
Ramalho-Santos, Miguel, et al., "*Stemness*": *Transcriptional Profiling of Embryonic* and *Adult Stem Cells*, Science Oct. 18, 2002:298(5593):597-600.
Fortunel, Nicolas et al., *Technical Comment on "Stemness": Transcriptional Profiling of Embryonic* and *Adult Stem Cells* and "*A Stem Cell Molecular Signature (I)*", Science Oct. 17, 2003:302(5644):393b.
Ivanova, Natalia et al., *Response to Comments on "Stemness": Transcriptional Profiling of Embryonic* and *Adult Stem Cells* and "*A Stem Cell Molecular Signature*", Science Oct. 17, 2003:302(5644):393d.
Metcalfe, Dean et al., *Mast Cells*, Physiological Reviews, vol. 77, No. 4, 1997.
Crawley, J.T.B., et al., "Distribution of Endothelial Cell Protein C/Activated Protein C Receptor (EPCR) During Mouse Embryo Development," Thromb. Haemost, 88-259-66 (2002).
Esmon, C.T., "Structure and functions of the endothelial cell protein C receptor," Crit. Care Med., 32(5):S298-S301 (2004).
Gu, J.M., et al., "*Disruption of the endothelial Cell Protein C Receptor Gene in Mice Causes Placental Thrombosis* and *Early Embryonic Lethality*," J. Biological Chemistry, 277(45):43335-43343(2002).
McNagny, K.M., et al., "*Thrombomucin, a Novel Cell Surface Protein that Defines Thrombocytes* and *Multipotent Hematopoietic Progenitors*," J. Cell Biology, 138(6):1395-1407 (1997).
Ghannadan et al., Int Arch Allergy Immunol, 127:299-307 (2002).
Goodell et al., J. Exp Med, 183:1797-1806 (1996).
Miyazato et al., Blood, 98:422-427 (2001).

* cited by examiner

*Primary Examiner* — Michail Belyavskyi
(74) *Attorney, Agent, or Firm* — Wolf, Greenfield & Sacks, P.C.

(57) ABSTRACT

Described herein are methods for purifying hematopoietic stem cells. Also described herein are methods for purifying EPCR+ cells. The invention also provides substantially pure isolated hematopoietic stems cells, including EPCR+ hematopoietic stem cells.

13 Claims, 6 Drawing Sheets

POPULATIONS OF HEMATOPOIETIC STEM CELLS

RELATED APPLICATION

This application is a continuation of U.S. application Ser. No.: 10/577,177, having a 371(c) date of Feb. 5, 2007, now U.S. Pat. No. 8,088,585, which is a national stage filing under 35 U.S.C. 371 of International Application PCT/US04/036143, filed Oct. 29, 2004, which claims the benefit of the filing date of U.S. provisional application No. 60/516,107, filed Oct. 31, 2003 entitled, "Methods for Purifying Hematopoietic Stem Cells," by Richard Mulligan and Alejandro Balazs. The teachings of the referenced applications are incorporated by reference in their entirety. International Application PCT/US04/036143 was published under PCT Article 21(2) in English.

FUNDING

The invention described herein was supported, in whole or in part, by grant SP50HL54785 from the National Institutes of Health. The United States government has certain rights in the invention.

BACKGROUND OF THE INVENTION

Mammalian blood cells provide for an extraordinarily diverse range of activities. The blood cells are divided into several lineages, including lymphoid, myeloid and erythroid. The lymphoid lineage, comprising B-cells and T-cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

Hematopoietic stem cells (HSC) represent a rare population of bone marrow cells with the capacity to reconstitute the entire hematopoietic system. See Jordan and Lemischka, 1990; Osawa et al., 1996. Present studies aimed at understanding the basic biology of these cells are undermined by an inability to obtain purified hematopoietic stem cells. Current purification of hematopoietic stem cells utilizes multicolor fluorescence activated cell sorting (FACS) to isolate subpopulations of bone marrow cells expressing a specific pattern of cell surface markers. In addition, hematopoietic stem cells possess unique dye efflux properties which create a distinct staining profile when stained with the vital dye Hoechst 33342. These weakly Hoechst stained cells, termed side-population (SP) cells, have been found to be greatly enriched for hematopoietic activity.

There is a strong interest to obtain purified hematopoietic stem cells. Having possession of such purified stem cell will allow for identification of growth factors associated with its self regeneration. The availability of purified hematopoietic stem cells would be extremely useful in bone marrow transplantation, as well as transplantation of other organs in association with the transplantation of bone marrow. Bone marrow transplantation alone has broad clinical implications for treatment for hematological malignancies, nonmalignant blood cell disorders, autoimmune diseases, and bone marrow failures associated with cancer treatment. In addition, HSC are important targets for gene therapy, where the inserted genes promote the health of the individual into whom the purified hematopoietic stem cells are transplanted.

SUMMARY OF THE INVENTION

The present invention provides methods for obtaining a substantially pure population of hematopoietic stem cells. The methods employ the use of Endothelial Protein C Receptor (EPCR) as a marker for hematopoietic stem cells. The methods comprise: contacting a biological sample containing cells with an affinity agent that binds to EPCR, followed by separating cells that bind to the affinity agent from cells that do not bind to the affinity agent. An EPCR antibody or fragment thereof can be used as an affinity agent to purify hematopoietic stem cells.

The present invention further provides substantially pure populations of hematopoietic stem cells.

BRIEF DESCRIPTION OF THE DRAWINGS

Embodiments of the invention are illustrated by way of example, and not by way of limitation, in the accompanying drawings.

DETAILED DESCRIPTION OF THE INVENTION

Figure 1:
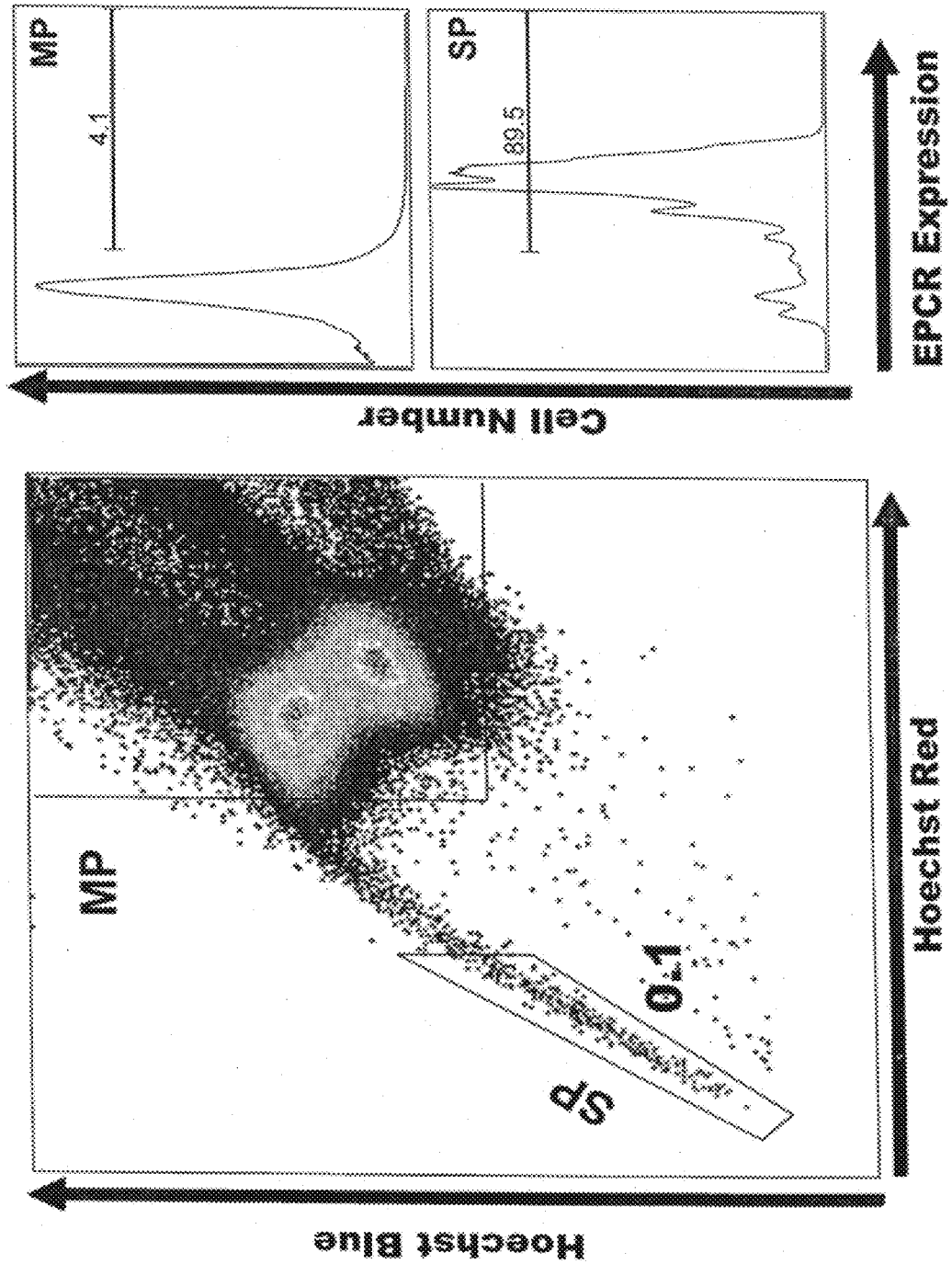
FIG. 1 shows that EPCR is detected at the cell-surface of SP cells by FACS.

Applicants have identified, for the first time, Endothelial Protein C Receptor
(EPCR) as a novel marker for hematopoietic stem cells. Applicants have demonstrated that using a single EPCR marker allows the purification of a substantially pure population of hematopoietic stem cells. These EPCR positive cells are functional stem cells capable of long-term engraftment to give rise to all blood lineages.

Accordingly, the present invention provides methods for obtaining a substantially pure population of hematopoietic stem cells, comprising: (1) contacting a biological sample comprising cells with an affinity agent which binds to EPCR under conditions appropriate for binding to occur; and (2) separating cells that bind to the affinity agent from cells that do not bind to the affinity agent, thereby producing a substantially pure population of hematopoietic stem cells.

The biological sample comprising cells may typically be a mixture of cells. The mixture of cells can be any solution of bone marrow cells, or other hematopoietic source. Initially, bone marrow cells may be obtained from a source of bone marrow, e.g., iliac crests, tibiae, femora, spine, or other bone cavities. Other sources of human hematopoietic stem cells include embryonic yolk sac, fetal liver, fetal and adult spleen, blood, including adult peripheral blood and umbilical cord blood.

For isolation of bone marrow from fetal bone or other bone source, an appropriate solution may be used to flush the bone, which solution will be a balanced salt solution, conveniently supplemented with fetal calf serum or other naturally occurring factors, in conjunction with an acceptable buffer at low concentration, such as from about 5-25 mM. Convenient buffers include Hepes, phosphate buffers and lactate buffers. Otherwise bone marrow may be aspirated from the bone in accordance with conventional ways.

The term "affinity agent", as used herein, refers to an agent that binds to EPCR expressed on a cell surface. Such an affinity agent may be recombinant, synthetic or naturally-derived, and may be a protein, a glycoprotein, a nucleic acid, a carbohydrate or a small molecule.

In one embodiment, the affinity agent that binds to EPCR is an EPCR antibody or fragment thereof. As used herein, the term "antibody" encompasses any antibody or fragment thereof, either native or recombinant, synthetic or naturally-derived, which retains sufficient specificity to bind specifically to EPCR, including the entire antibody and antibody fragments containing functional portions thereof. The term "antibody" includes any monospecific or bispecific compound comprised of a sufficient portion of the light chain variable region and/or the heavy chain variable region to effect binding to the epitope to which the whole antibody has binding specificity. The fragments can include the variable region of at least one heavy or light chain immunoglobulin polypeptide, and include, but are not limited to, Fab fragments, F(ab').sub.2 fragments, and Fv fragments. The EPCR antibodies may be obtained by methods known in the art for production of antibodies or functional portions thereof.

In another embodiment, the affinity agent that binds to EPCR is an antibody mimic. For example, Lipovsek et al. describe a new family of proteins capable of evolving to bind any compound of interest. See PCT Application WO2001US0006414, filed Feb. 28, 2001, published as WO 0164942. These proteins, which make use of a fibronectin or fibronectin-like scaffold, function in a manner characteristic of natural or engineered antibodies (that is, polyclonal, monoclonal, or −2 single-chain antibodies) and, in addition, possess structural advantages. These antibody mimics may be used to design proteins capable of binding to EPCR. In particular, the fibronectin-based molecules described may be used as scaffolds which are subjected to directed evolution designed to randomize one or more of the three fibronectin loops which are analogous to the complementarity-determining regions (CDRs) of an antibody variable region. Such a directed evolution approach results in the production of antibody-like molecules with high affinities for antigens of interest. In addition, the scaffolds described herein may be used to display defined exposed loops (for example, loops previously randomized and selected on the basis of antigen binding) in order to direct the evolution of molecules that bind to such introduced loops. A selection of this type may be carried out to identify recognition molecules for any individual CDR-like loop or, alternatively, for the recognition of two or all three CDR-like loops combined into a non-linear epitope.

In an alternative embodiment, the affinity agent that binds EPCR may be a protein or a small peptide that binds to EPCR. Such protein or small peptide may be an EPCR ligand, interacting protein, or any functional variants or fragments thereof. The variants may be naturally arising or may be artificially created. EPCR ligands or other binding proteins may be identified using methods known in the art, including, for example, two-hybrid system, immunoprecipitation, affinity purification, etc. The affinity agent may also be a chimeric fusion protein containing at least one EPCR-binding moiety, produced in accordance with techniques that are well known to those skilled in the art.

In another embodiment, the affinity agent that binds EPCR may be an aptamer that binds to EPCR. An aptamer is a double- or single-stranded DNA or single-stranded RNA molecule that binds to specific polypeptide targets. See Hermann and Patel, 2000; and Burgstaller et al., 2002, and references therein. Such aptamers may be selected in vitro from libraries containing random sequences of up to a few hundred nucleotides using EPCR or a portion thereof as a probe.

In a further embodiment, the affinity agent that binds EPCR may be a small molecule. Such small molecules can be obtained by screening libraries of small molecules with EPCR as a probe. For example, a high-density microarray of small molecules generated by diversity-oriented synthesis described by Kuruvilla et al. may be used to screen for small molecules that bind EPCR. See Kuruvilla, et al., 2002.

Various techniques may be employed to separate the mixture of cells. Such techniques include, for example, magnetic separation, antibody-coated magnetic beads, column chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique.

Separation techniques that can be used include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342).

Techniques providing accurate separation include fluorescence activated cell sorters, which can have varying degrees of sophistication, e.g., a plurality of color channels, low angle and obtuse light scattering detecting channels, impedance channels, etc.

In one embodiment, the EPCR marker may be used alone to purify hematopoietic stem cells. Alternatively, in another embodiment, the EPCR marker may be used in conjunction with other hematopoietic stem cell markers to purify hematopoietic stem cells. For example, CD34 antigen is known to be expressed on human hematopoietic stem cells. See Andrews et al., J. Exp. Med. 169: 1721-1731 (1989); Civin, U.S. Pat. No. 4,965,204, issued Oct. 23, 1990; Civin, European Patent Application 395355, published Oct. 31, 1990. Accordingly, CD34 antibodies or fragments thereof can be used to purify human hematopoietic stem cells in conjunction with EPCR antibodies. The EPCR marker and other marker(s) may be used, either simultaneously or sequentially, to separate cells. When the markers are used sequentially, the particular order of separation is not critical to this invention.

In a further embodiment, a biological sample comprising cells may first be subject to an initial crude separation to remove a portion of differentiated cells prior to the purification by EPCR antibodies. For example, magnetic bead separations may be used initially to remove large numbers of lineage committed cells, namely major cell populations of the hematopoietic systems, including such lineages as T-cells, B-cells, (both pre-B and B-cells), myelomonocytic cells, or minor cell populations, such as megakaryocytes, mast cells, eosinophils and basophils. By removing a large proportion of differentiated cells, the number of dedicated cells present in the next stage of purification is minimized.

The present invention also provides a substantially pure population of hematopoietic stem cells isolated by methods of the invention.

Hematopoietic stem cells purified according to the methods of the present invention may find use in a variety of ways. They can be used to reconstitute an irradiated host and/or a host who has received chemotherapy; or as a source of cells for specific lineages, by providing for their maturation, proliferation and differentiation into one or more selected lineages by employing a variety of factors, such as erythropoietin, colony stimulating factors, e.g., GM-CSF, G-CSF, or M-CSF, interleukins, e.g., IL-1, -2, -3, -4, -5, -6, -7, -8, etc., Leukemia Inhibitory Factory (LIF), Steel Factor (Stl), or the like, or stromal cells associated with the stem cells becoming committed to a particular lineage, or with their proliferation, maturation and differentiation. The stem cells may also be used in the isolation and evaluation of factors associated with the differentiation and maturation of hematopoietic cells. Thus, the stem cells may be used in assays to determine the activity of media, such as conditioned media, evaluate fluids for cell growth activity, involvement with dedication of particular lineages, or the like.

The stem cells may be used for the treatment of genetic diseases. Genetic diseases associated with hematopoietic cells may be treated by genetic modification of autologous or allogeneic stem cells to correct the genetic defect. For example, diseases such as B-thalassemia, sickle cell anemia, adenosine deaminase deficiency, recombinase deficiency, recombinase regulatory gene deficiency, etc. may be corrected by introduction of a wild-type gene into the stem cells, either by homologous or random recombination. With allogeneic stem cells, normal cells lacking the genetic defect can be used as a therapy. Other indications of gene therapy are introduction of drug resistance genes to enable normal stem cells to have an advantage and be subject to selective pressure, e.g., the multiple drug resistance gene (MDR). Diseases other than those associated with hematopoietic cells may also be treated, where the disease is related to the lack of a particular secreted product such as a hormone, enzyme, interferon, factor, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

Alternatively, one may wish to remove a particular variable region of a T-cell receptor from the T-cell repertoire. By employing homologous recombination, or antisense or ribozyme sequence which prevents expression, the expression of the particular T-cell receptor may be inhibited. For hematotropic pathogens, such as HIV, HTLV-I and II, etc. the stem cells could be genetically modified to introduce an antisense sequence or ribozyme which would prevent the proliferation of the pathogen in the stem cell or cells differentiated from the stem cells. Methods for recombination in mammalian cells may be found in Molecular Cloning, A Laboratory Manual (1989) Sambrook, Fritsch and Maniatis, Cold Spring Harbor, N.Y.

The hematopoietic stem cells, either autologous or allogeneic, may be used for treatment of various diseases where toxic therapies may be involved. For example, in the treatment of neoplasia, bone marrow may be removed from the patient (autologous) or from a "matched" donor ("allogeneic") and the stem cells isolated and optimally frozen. The patient's bone marrow may be partially or wholly ablated using irradiation and/or chemotherapy. Once the treatment is completed, the stem cells may be thawed, if appropriate, administered to the patient by any convenient means, e.g., intravascularly, in a physiologically acceptable medium. The patient may then be monitored for signs of engraftment.

The hematopoietic stem cells obtained by the methods of the present invention can be used immediately or frozen at liquid nitrogen temperatures and stored for long periods of time, being thawed and capable of being reused. The stem cells, either used immediately or thawed, may be expanded by being grown in culture. In this way, one can repetitively administer stem cells during a course of a toxic therapy. The stem cells may be expanded by growing in conditioned medium from stromal cells, such as stromal cells that can be obtained from bone marrow, fetal thymus or fetal liver, and are shown to provide for the secretion of growth factors associated with stem cell maintenance, coculturing with such stromal cells, or in medium comprising maintenance factors supporting the proliferation of stem cells, where the stromal cells may be allogeneic or xenogeneic. Before using in the coculture, the mixed stromal cell preparations may be freed of hematopoietic cells employing appropriate monoclonal antibodies for removal of the undesired cells, e.g., with antibody-toxin conjugates, antibody and complement, etc. Alternatively, cloned stromal cell lines may be used where the stromal lines may be allogeneic or xenogeneic.

The present invention also provides methods for obtaining a substantially pure population of EPCR+ cells, comprising: (1) contacting a biological sample comprising cells with an antibody or fragment thereof which binds to endothelial protein C receptor (EPCR) under conditions appropriate for binding to occur; and (2) separating cells that bind to the antibody or fragment from cells that do not bind to the antibody or fragment, thereby producing a substantially pure population of EPCR+ cells.

The present invention further provides a substantially pure population of EPCR+ cells.

The practice of the present invention will employ, unless otherwise indicated, conventional techniques of stem cell biology, mouse genetics, developmental biology, cell biology, cell culture, molecular biology, transgenic biology, microbiology, recombinant DNA, and immunology, which are within the skill of the art. Such techniques are described in the literature. All patents, patent applications and references cited herein are incorporated in their entirety by reference.

One skilled in the art readily appreciates that the present invention is well adapted to carry out the objects and obtain the ends and advantages mentioned, as well as those inherent therein. The methods, systems and kits are representative of preferred embodiments, are exemplary, and are not intended as limitations on the scope of the invention. Modifications therein and other uses will occur to those skilled in the art. These modifications are encompassed within the spirit of the invention and are defined by the scope of the claims. It will be readily apparent to a person skilled in the art that varying substitutions and modifications may be made to the invention disclosed herein without departing from the scope and spirit of the invention.

EXEMPLIFICATION

The invention now being generally described, it will be more readily understood by reference to the following examples, which are included merely for purposes of illustration of certain aspects and embodiments of the present invention, and are not intended to limit the invention.

EXAMPLE 1

Identification of EPCR as an HSC Marker

In an effort to catalogue the expression profile of highly purified stem cells, microarray analysis of HSC was performed on a population of murine HSC purified using both cell surface markers and Hoechst dye staining. The expression profile of this population was compared to that of a non-stem cell population to determine genes specific for HSC. Endothelial Protein C Receptor (EPCR) was found to be expressed over 40 fold higher in HSC over non-HSC populations. The receptor, previously described only on the surface of endothelial cells of large vessels, is involved in the anti-coagulation response by activating protein C in the blood which cleaves factor Va and VIIIa which in turn prevents the cleavage of prothrombin and inhibits clotting. Previous studies by others have not described EPCR as a hematopoietic stem cell marker.

Figure 2:
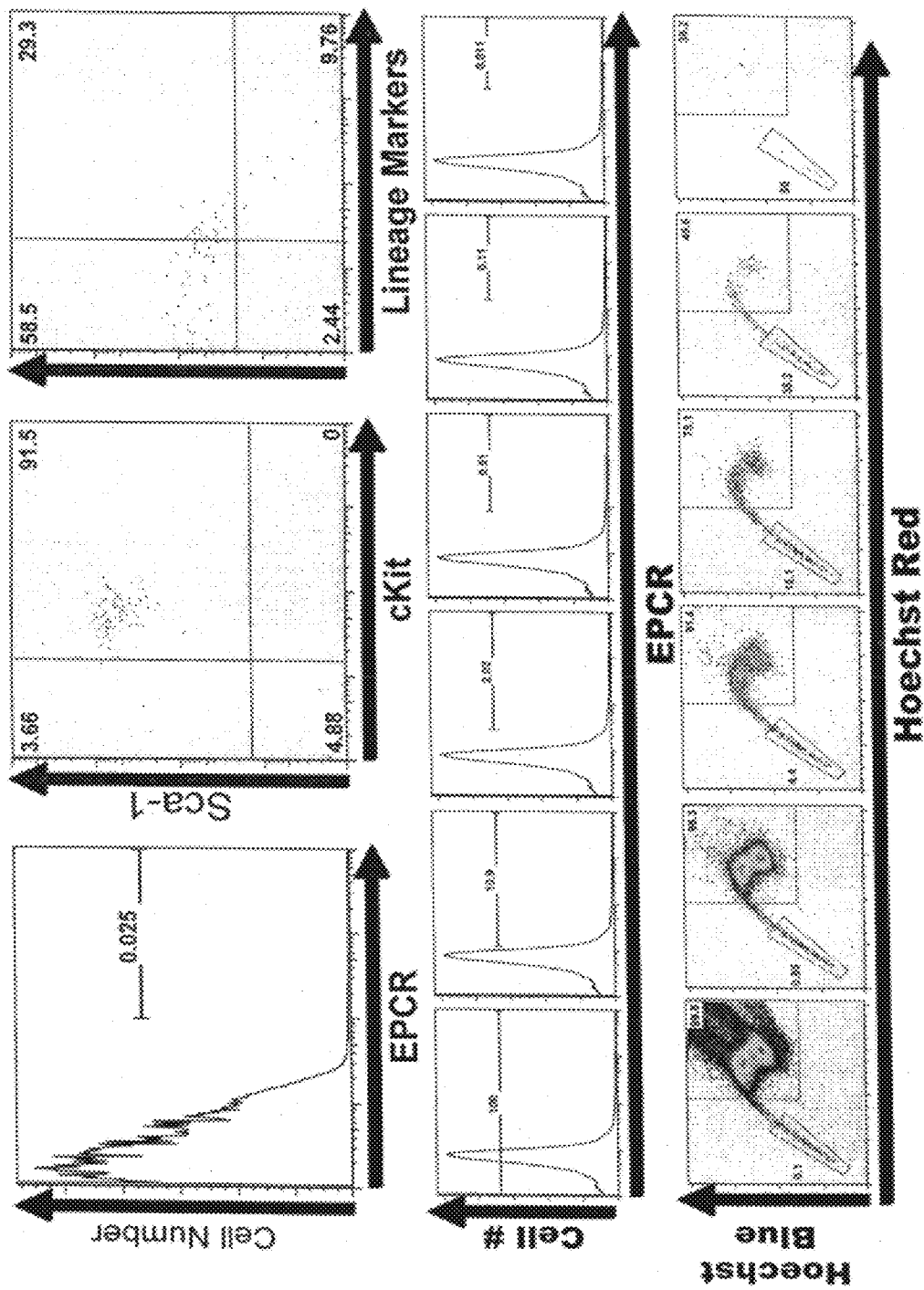
FIG. 2 shows that EPCR positive cells are Sca-1Hi, cKit+, and lineage marker negative.
Figure 3:
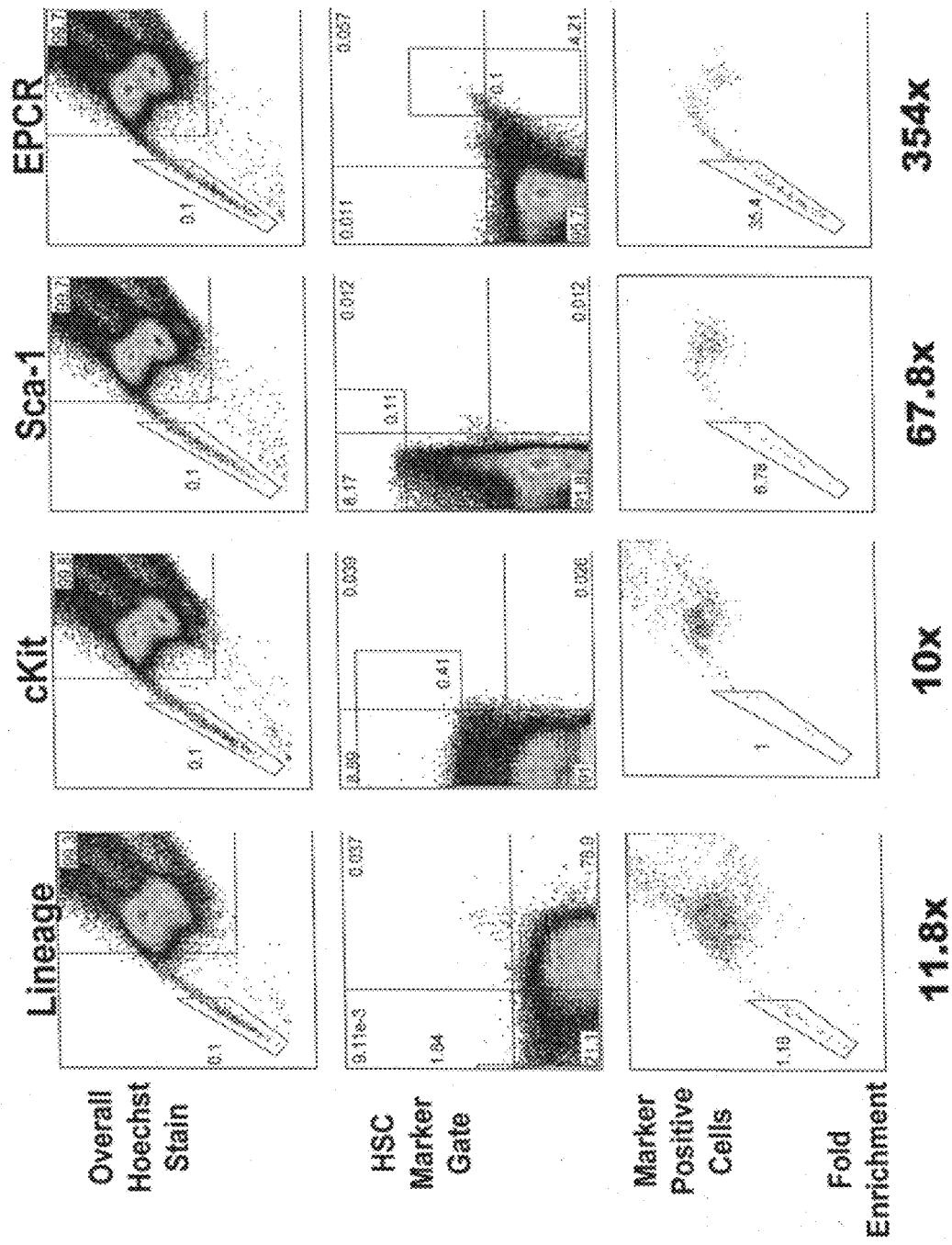
FIG. 3 shows that EPCR enriches for SP more than any other single marker.
Figure 4:
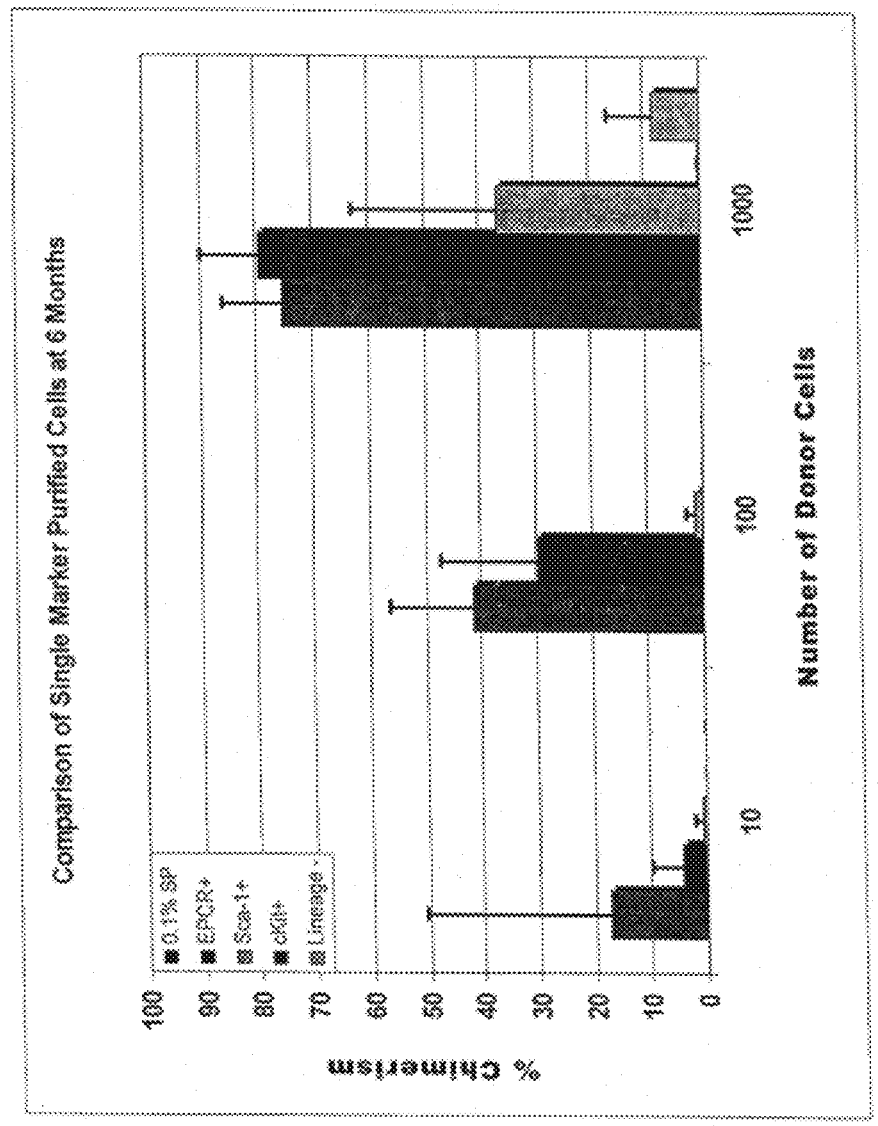
FIG. 4 shows EPCR purified HSCs that engraft in a competitive repopulation assay.
Figure 5:
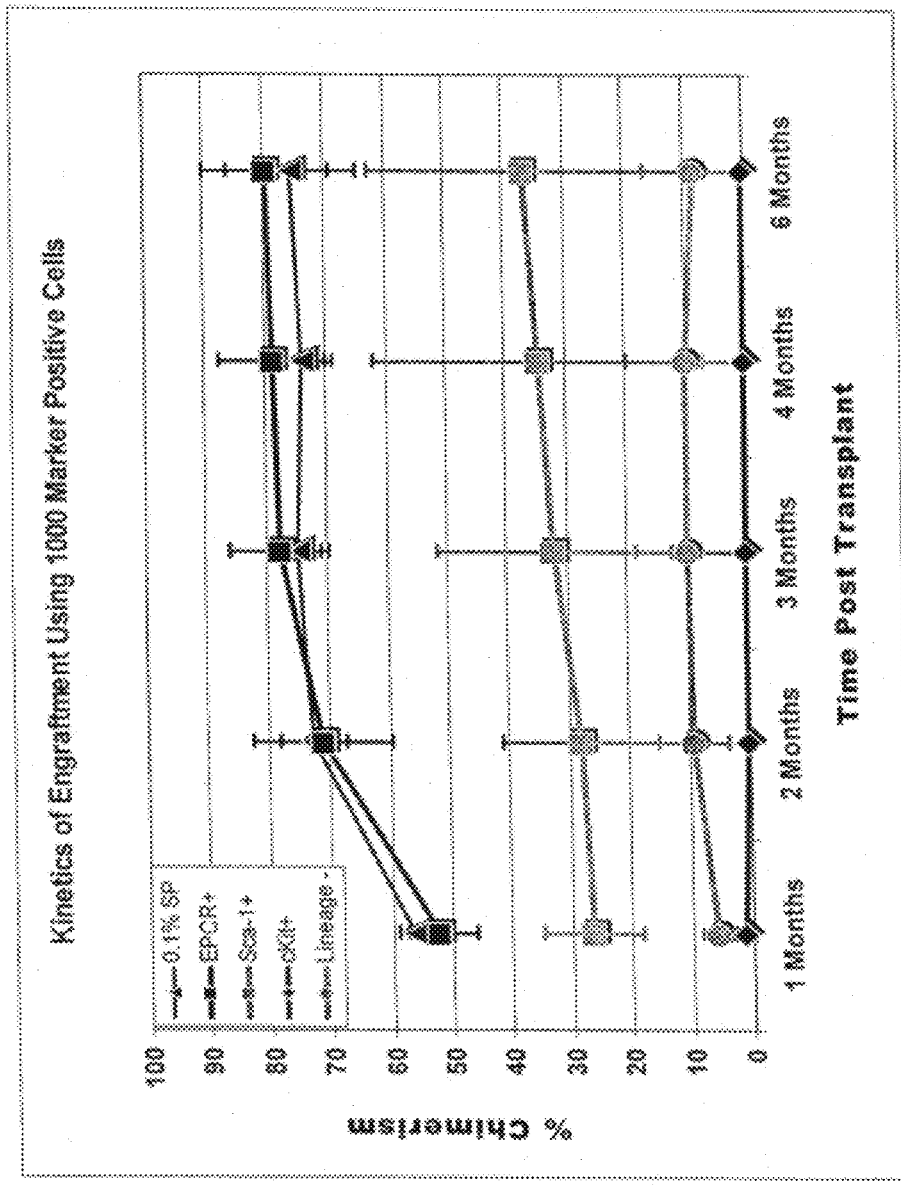
FIG. 5 shows that EPCR purified HSCs are capable of long term engraftment.
Figure 6:
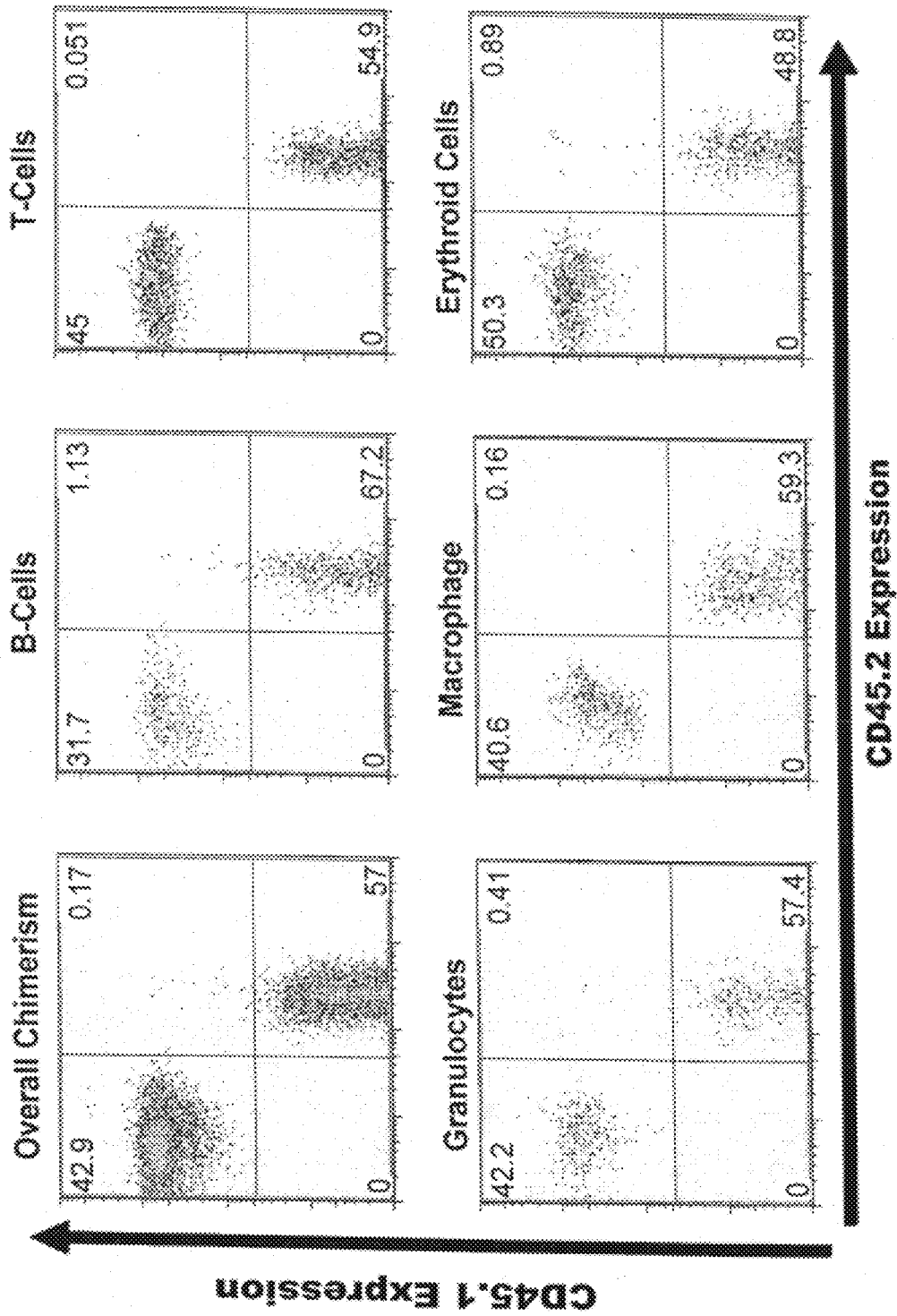
FIG. 6 shows that EPCR purified HSCs are capable of engrafting all blood lineages.

Applicants demonstrate here that EPCR can be used as a marker for HSC purification, based on the following findings. EPCR is detected at the cell-surface of SP cells by FACS (See FIG. 1). EPCR positive cells are Sca-1Hi, cKit+, and lineage marker negative, lending support to the notion that EPCR is a HSC marker (See FIG. 2). Furthermore, EPCR appears to be a better HSC marker than other known single HSC marker, as EPCR-based purification enriches for SP more than any other known single HSC marker (See FIG. 3). Cell sorted by EPCR expression alone appears to be functional HSC, as demonstrated by FIG. 4-6. FIG. 4 shows that cells sorted by EPCR expression alone are comparable to SP cells in their ability to engraft lethally irradiated mice and better than any other single marker tested. FIG. 5 shows that bone marrow transplantation using EPCR positive cells showed significant and long-term engraftment. FIG. 6 shows that engraftment of EPCR positive cells contributed equally to all blood lineages.

Methods

Fluorescence Activated Cell Sorting:

Analysis and sorting was performed on a triple laser MoFlo (Cytomation, CO) using the Summit software. Hoechst 33342 was excited at 351 nm, and fluorescence emission was detected using 405/BP30 and 570/BP20 optical filters against Hoechst blue and Hoechst red respectively and a 555-nm long-pass dichroic mirror (all from Omega Optical Inc.) to separate emission wavelengths. Both Hoechst blue and red fluorescence were acquired on a linear scale. PI fluorescence was measured through a 630BP30 filter after being excited by a 488 nm Argon laser. A live gate was defined as the cells negative for PI allowing dead cells to be excluded.

Competitive Repopulation Assays:

5-6 week old recipient C57BL/6J (CD45.2) mice were lethally irradiated with 1300 rads in two 650 rad doses 3 hours apart and were transplanted by retro-orbital injection the following day. Donor B6.SJL-PtprcaPep3b/BoyJ (CD45.1) mice expressing the Ly5.1 isoform of the CD45 marker were sacrificed by asphyxiation and their femur and tibiae crushed with a mortar and pestle. Samples for SP sorting were stained at a cell density of 4×106 cells/mL with 10 mg/mL Hoechst 33342 dye. Cells were subjected to a ficoll gradient to isolate lymphocytes prior to staining with monoclonal antibodies against surface antigens. Staining was performed using a monoclonal antibody against mouse EPCR followed by detection with secondary antibody against rat IgG conjugated to Alexaflour-488 (Molecular Probes, OR). Antibodies against Sca-1, cKit, and Lineage markers were obtained from BD Pharmingen. After staining, cells were washed and resuspended in media containing Propidium Iodide to exclude dead cells by FACS. Sorted donor cells were transplanted with 2×105 competitor cells from a C57BL/6J recipient littermate. Blood samples were taken each month following transplantation and chimerism measured by flow cytometry using antibodies specific for each isoform of the CD45 receptor.

Analysis of Multi-Lineage Engraftment:

Blood was taken from a representative animal transplanted with 1000 EPCR+ cells 6 Months post-transplant and stained using monoclonal antibodies against CD45.1 conjugated to Phycoerythrin, CD45.2 conjugated to Fluorescein and one of the following Biotinylated Lineage Antibodies: Anti-B220 (B-Cells), Anti-CD3e (T-Cells), Anti-Gr-1 (Granulocytes), Anti-Mac-1 (Macrophage) or Anti-Ter119 (Erythroid Cells). After washing, samples were stained with Streptavidin labelled APC and analyzed using a FACSCalibur (Beckton Dickinson, CA). The ratio of CD45.1 to CD45.2 expressing cells within each subset of lineage positive cells was determined using FlowJo (Treestar, CA) analysis software.

References

Burgstaller, P., et al., (2002). Aptamers and aptazymes: accelerating small molecule drug discovery. Curr. Opin. Drug Discov. Devel. 5: 690-700.

Herman T., Patel, D.J., (2000). Adaptive recognition by nucleic acid aptamers. Science 287: 820-5.

Jordan, C. T. and Lemischka, I. R. (1990). Clonal and systemic analysis of long-term hematopoiesis in the mouse. Genes Dev. 4: 220-232

Kuruvilla, F. G., et al., (2002). Dissecting glucose signalling with diversity-oriented synthesis and small-molecule microarrays. Nature, 416: 653-657.

Osawa, M et al., (1996). Long-term lymphohematopoietic reconstitution by a single CD34-low/negative hematopoietic stem cell. Science 273: 242-245.

Zhong, R. K., et al., (1996) Distinct developmental patterns of short-term and long-term functioning lymphoid and myeloid precursors defined by competitive limiting dilution analysis in vivo. J. Immunol. 157: 138-145.

What is claimed is:

1. A population of hematopoietic stem cells consisting of EPCR+ cells produced by a method comprising:
   contacting a biological sample comprising cells with an affinity agent which binds to endothelial protein C receptor (EPCR) under conditions appropriate for binding to occur; and
   separating cells that bind to the affinity agent from cells that do not bind to the affinity agent, thereby producing a population of hematopoietic stem cells consisting of EPCR+ cells.

2. The population of hematopoietic stem cells of claim 1, wherein the affinity agent is an antibody or fragment thereof.

3. The population of hematopoietic stem cells of claim 1, wherein the step of separating cells is performed by a method selected from the group consisting of: column chromatography, fluorescence-activated cell sorting, magnetic bead separation and direct immune adherence.

4. The population of hematopoietic stem cells of claim 1, wherein the biological sample comprising cells is selected from the group consisting of: bone marrow cells, embryonic yolk sac, fetal liver, fetal and adult spleen and blood.

5. A population of hematopoietic stem cells consisting of EPCR+ cells.

6. The population of hematopoietic stem cells of claim 5, wherein the EPCR+cells are human EPCR+ cells.

7. The population of hematopoietic stem cells of claim 5, wherein the EPCR+cells are murine EPCR+ cells.

8. A composition comprising (a) a population of hematopoietic stem cells consisting of EPCR+cells and (b) a physiologically acceptable medium.

9. The composition of claim 8, wherein the EPCR+ cells are human EPCR+ cells.

10. The composition of claim 8, wherein the EPCR+ cells are murine EPCR+ cells.

11. A population of hematopoietic stem cells, which consisting of EPCR+ cells, in a physiologically acceptable medium.

12. The population of hematopoietic stem cells of claim 11, wherein the EPCR+ cells are human EPCR+ cells.

13. The population of hematopoietic stem cells of claim 11, wherein the EPCR+ cells are murine EPCR+ cells.

* * * * *

UNITED STATES PATENT AND TRADEMARK OFFICE
CERTIFICATE OF CORRECTION

| | | |
|---|---|---|
| PATENT NO. | : 8,586,100 B2 | Page 1 of 1 |
| APPLICATION NO. | : 13/298724 | |
| DATED | : November 19, 2013 | |
| INVENTOR(S) | : Balazs et al. | |

It is certified that error appears in the above-identified patent and that said Letters Patent is hereby corrected as shown below:

In the Claims:
Column 9, claim 11, line 1-2, please change "which consisting of" to --consisting of--.

Signed and Sealed this
Fourth Day of February, 2014

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,586,100 B2 |
| APPLICATION NO. | : 13/298724 |
| DATED | : November 19, 2013 |
| INVENTOR(S) | : Alejandro Balazs et al. |

It is certified that error appears in the above-identified patent and that said Letters Patent is hereby corrected as shown below:

In the Specification

At Column 1, Line 19, please replace the paragraph titled "FUNDING" with the following paragraph:
FEDERALLY SPONSORED RESEARCH
This invention was made with government support under Grant Number HL054785, awarded by the National Institutes of Health. The Government has certain rights in the invention.

Signed and Sealed this
Sixth Day of June, 2023

Katherine Kelly Vidal
*Director of the United States Patent and Trademark Office*